United States Patent [19]
Farina et al.

[11] Patent Number: 4,873,328
[45] Date of Patent: Oct. 10, 1989

[54] PROCESS FOR PREPARING ALKOXYALKYLIDENEHYDRAZINOPYRIDAZINE DERIVATIVES

[75] Inventors: Carlo Farina, Como; Mario Pinza, Milan; Alberto Cerri, Pavia; Francesco Parravicini, Milan, all of Italy

[73] Assignee: I.S.F. Societa Per Azioni, Milan, Italy

[21] Appl. No.: 140,850

[22] Filed: Jan. 5, 1988

[30] Foreign Application Priority Data

Jan. 8, 1987 [IT] Italy ............................... 19026 A/87

[51] Int. Cl.$^4$ .................... C07D 237/21; A61K 31/50
[52] U.S. Cl. ..................................... 544/239; 544/238
[58] Field of Search ......................... 544/239; 540/238

[56] References Cited

U.S. PATENT DOCUMENTS

| 4,324,788 | 4/1982 | Dorigotti et al. | 424/250 |
| 4,575,552 | 3/1986 | Farina et al. | 544/224 |

*Primary Examiner*—Nicholas S. Rizzo
*Attorney, Agent, or Firm*—Nancy S. Mayer; Janice E. Williams; Alan D. Lourie

[57] ABSTRACT

A novel process for preparing alkoxyalkylidenehydrazinopyridazine derivatives which comprises reducing a novel alkoxytriphenylmethylazopyridazine derivative, removing the triphenylmethyl group and reacting with an aldehyde or ketone derivative.

A specific compound produced by this process is 3-[3-[[2-(3,4-dimethoxyphenyl)ethyl]amino]-2-hydroxypropoxy]-6-isopropylidenehydrazinopyridazine.

5 Claims, No Drawings

PROCESS FOR PREPARING ALKOXYALKYLIDENEHYDRAZINOPYRIDAZINE DERIVATIVES

The present invention relates to an improved process for preparing alkoxyalkylidenehydrazinopyridazine derivatives which have antihypertensive activity. Specifically this invention relates to an improved process for preparing 3-[3-[[2-(3,4-dimethoxyphenyl)ethyl]amino]-2-hydroxypropoxy]-6-isopropylidenehydrazinopyridazine either as a racemic mixture or in an enantiomerically enriched form.

In U.S. Pat. No. 4324788 a process for preparing cmpounds of the formula (1) is described:

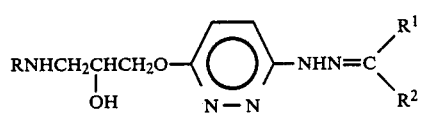
(1)

wherein
R is alkyl or cycloalkyl having up to 5 carbon atoms, optionally substituted with one of the following: unsubstituted phenyl, phenyl substituted by one, two or three $C_{1-3}$alkoxy substituents or a methylenedioxy group, or cycloalkyl;
$R^1$ is hydrogen or $C_{1-3}$alkyl; and
$R^2$ is $C_{1-3}$alkyl, carboxy or phenyl,
which process comprises the reaction of 3,6-dichloropyridazine with isopropylidene glycerol in the presence of a base to form a compound of the formula (2):

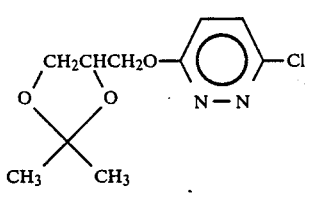
(2)

which is successively treated with hydrazine and $R^1R^2CO$ wherein $R^1$ and $R^2$ are as hereinbefore defined to form a compound of the formula (3):

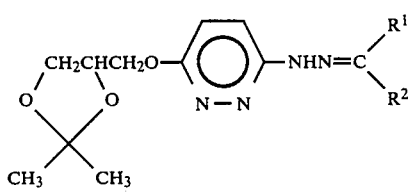
(3)

followed by subsequent processing to afford compounds of the formula (I) in overall yields of about 2–4% from 3,6-dichloropyridazine.

A disadvantage of this process is that displacement of the relatively unreactive chloro group of the compound of the formula (2) with hydrazine requires high temperatures and high concentrations of hydrazine. Such harsh conditions are not particularly selective and hydrazine can displace the chloro group, or the 2,2-dimethyl-1,3-dioxolane-4-methoxy group or both these groups resulting in a complex reaction mixture and a low yield of a compound of the formula (3).

We have now found that compounds of the formula (4):

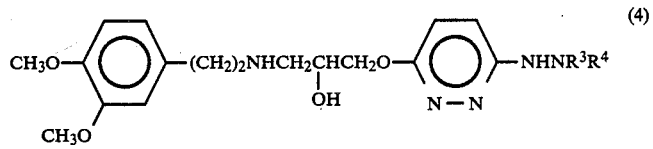
(4)

wherein
$R^3$ and $R^4$ are both hydrogen or together are $=CR^1R^2$
where
$R^1$ is hydrogen or $C_{1-3}$alkyl and
$R^2$ is $C_{1-3}$alkyl, carboxy or phenyl,
can be prepared from 3,6-dichloropyridazine in very high yields via reactions which occur under extremely mild conditions of temperature and pressure.

Accordingly the present invention provides a process for preparing compounds of the formula (4) and pharmaceutically acceptable salts thereof which process comprises:
reducing a compound of the formula (5):

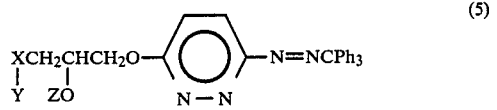
(5)

wherein
X is

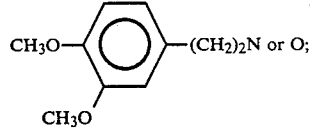

Y and Z are both hydrogen or
Y and Z together are a protecting group:

wherein $R^5$ is hydrogen or $C_{1-3}$alkyl and $R^6$ is $C_{1-3}$alkyl or phenyl, and
Ph is phenyl,
to afford a compound of the formula (6):

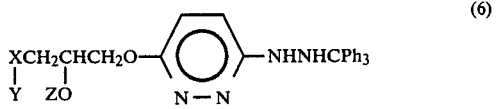
(6)

wherein Ph, X, Y and Z are as hereinbefore defined,
and thereafter:
(i) removing the triphenylmethyl group and any other protecting groups to afford a compound of the formula (7) or a salt thereof:

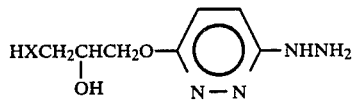 (7)

wherein x is as hereinbefore defined,
(ii) when X is

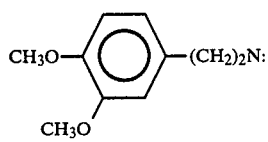

optionally reacting with $R^1R^2CO$ wherein $R^1$ and $R^2$ are as hereinbefore defined to yield a compound of the formula (4);
or when X is O:
reacting with $R^1R^2CO$ wherein $R^1$ and $R^2$ are as hereinbefore defined to afford a compound of the formula (8):

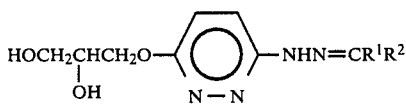 (8)

wherein $R^1$ and $R^2$ are as hereinbefore defined which is converted to a compound of the formula (9):

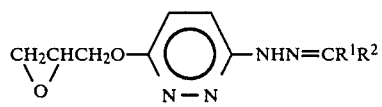 (9)

wherein $R^1$ and $R^2$ are as hereinbefore defined which is reacted with 3,4-dimethoxyphenethylamine, and thereafter optionally removing the $CR^1R^2$ group by hydrolysis, and
(iii) optionally forming a pharmaceutically acceptable salt.

In a compound of the formula (5) suitably X is O and Y and Z are both hydrogen.
More suitably X is O and Y and Z are together a protecting group:

Preferably X is

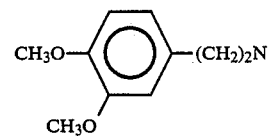

and Y and Z are together a protecting group:

Particularly X is

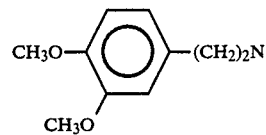

and Y and Z are both hydrogen. With these meanings of X, Y, and Z a compound of the formula (5) can be converted under mild conditions to a compound of the formula (4) of high purity and in high yield.

Examples of $C_{1-3}$alkyl in the groups $R^5$ and $R^6$ are methyl, ethyl, propyl and iso-propyl. Suitably $R^5$ is hydrogen and $R^6$ is iso-propyl or phenyl or $R^5$ and $R^6$ are both methyl.

Suitably a compound of the formula (5) is reduced to a compound of the formula (6) by hydrogenation with palladium on carbon in a solvent such as a $C_{1-4}$alkanol, for example ethanol, at a temperature from 0° to 50° C. and at non-extreme pressures, preferably at room temperature and at atmospheric pressure.

Alternatively other reducing agents can be employed, for example sodium borohydride with palladium on carbon, sodium hydrosulphite or an aqueous mixture of stannous chloride and sodium hydroxide, in a solvent such as a $C_{1-4}$alkanol or tetrahydrofuran, suitably in a mixture of ethanol and tetrahydrofuran, at a temperature from 0° to 50° C., preferably at room temperature.

Protecting groups can be removed from a compound of the formula (6) in conventional manner as described for example in "Protective Groups in Organic Synthesis, T. W. Greene, John Wiley & Sons (1981)". Suitably the triphenylmethyl and $CR^5R^6$ groups are both cleaved by acid-catalysed hydrolysis to afford a compound of the formula (7), which can be isolated as a free base or an acid-addition salt thereof.

The reaction of a compound of the formula (7) or a salt thereof with $R^1R^2CO$ is conveniently performed in a solvent such as a $C_{1-4}$alkanol, suitably methanol preferably aqueous methanol, at an elevated temperature, preferably at the reflux temperature of the reaction mixture. Examples of $R^1R^2CO$ are acetone, benzaldehyde, iso-butyraldehyde and pyruvic acid. Suitably an excess quantity of $R^1R^2CO$ is used, for example from 1.1 to 3 molar equivalents. When $R^1R^2CO$ is acetone, the reagent can be added in large excess as a co-solvent.

A compound of the formula (7) need not be isolated. For example preferably a compound of the formula (6) wherein X is

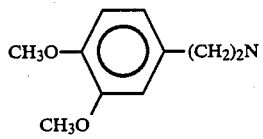

and Y and Z are both hydrogen is treated with a mixture of hydrochloric acid, methanol and acetone to afford directly a compound of the formula (4) wherein $R^1$ and $R^2$ are both methyl, which is preferably isolated as the dihydrochloride salt.

Suitably a compound of the formula (8) is converted to a compound of the formula (9) by treatment with hydrogen bromide in acetic acid, followed by treatment with a base such as aqueous sodium hydroxide in a suitable solvent such as dichloromethane preferably in the presence of a phase transfer catalyst such as a quaternary ammonium salt, e.g. cetyltrimethylammonium bromide.

Suitably the reaction of a compound of the formula (9) with 3,4-dimethoxyphenethylamine is performed in the absence of a solvent or in a suitable solvent such as a $C_{1-4}$alkanol, at a temperature from 30° to 100° C. Preferably a compound of the formula (9) and 3,4-dimethoxyphenethylamine are fused together at 50° C.

A compound of the formula (4) wherein $R^3$ and $R^4$ are together $CR^1R^2$ can be converted to a a compound of the formula (4) wherein $R^3$ and $R^4$ are both hydrogen by acid-catalysed hydrolysis, suitably by treatment with dilute hydrochloric acid.

The compounds of the formula (4) can form pharmaceutically acceptable salts with either organic or inorganic acids, for example those formed with hydrochloric, hydrobromic, hydroiodic, methanesulphonic, sulphuric, maleic, fumaric, succinic, acetic, tartaric, citric and lactic acids.

Pharmaceutically acceptable salts can be prepared in conventional manner, for example they may be prepared by treating the free base with the appropriate acid in a $C_{1-4}$alkanol, or they can be prepared by the use of an ion-exchange resin to form the desired salt directly from the free base or via a different acid addition salt.

In a further aspect the present invention provides a process for preparing a compound of the formula (5) which comprises reacting in the presence of a stronge base a compound of the formula (10):

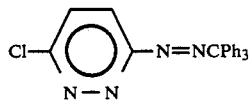

(10)

with a compound of the formula (11):

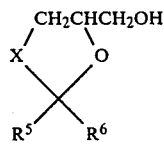

(11)

wherein Ph, X, $R^5$ and $R^6$ are as hereinbefore defined and thereafter optionally removing the $CR^5R^6$ protecting group.

Examples of strong bases include sodium hydride, potassium hydride and potassium t-butoxide. Suitably when sodium hydride is used the reaction is performed in a solvent such as toluene or acetonitrile. When the base used is potassium t-butoxide conveniently the reaction is performed in t-butanol with a co-solvent such as dichloromethane. Suitably the reaction is performed between −10° and 40° C., preferably between 0° and 25° C.

Suitably a compound of the formula (5) wherein Y and Z together are $CR^5R^6$ is isolated and optionally is hydrolysed by treatment with acid to afford a compound of the formula (5) wherein Y and Z are both hydrogen. Alternatively a compound of the formula (5) wherein Y and Z together are $CR^5R^6$ is not isolated but is hydrolysed in situ by treatment with an acid, for example with hydrochloric acid at room temperature to afford a compound of the formula (5) wherein Y and Z are both hydrogen.

A compound of the formula (10) can be prepared by the oxidation of 3-chloro-6-(2-triphenylmethylhydrazino)pyridazine with an oxidising agent such as potassium permanganate, potassium dichromate or sodium hypochlorite as described in U.S. Pat. No. 4575552. Preferably the oxidation is performed with aqueous sodium hydrochlorite in a suitable solvent such as a halohydrocarbon e.g. dichloromethane in the presence of a phase transfer catalyst such as cetyltrimethylammonium bromide at a temperature from 0° to 40° C., conveniently at room temperature.

A compound of the formula (11) wherein X is

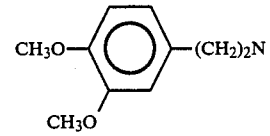

can be prepared as described in EPA-7448 and GB 1591723 by reacting a compound of the formula (12):

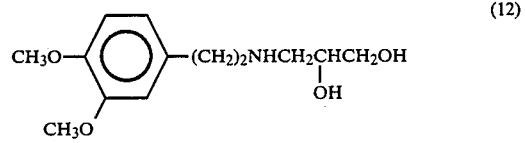

(12)

with $R^5R^6CO$ wherein $R^5$ and $R^6$ are as hereinbefore defined or a chemical equivalent thereof.

Examples of $R^5R^6CO$ or a chemical equivalent thereof include iso-butyraldehyde, benzaldehyde and 2,2-dimethoxypropane. Suitably the reaction is performed in a solvent such as dichloromethane or toluene, optionally in the presence of an acid catalyst such as p-toluenesulphonic acid, at an elevated temperature, preferably at the reflux temperature of the solvent. Conveniently the reaction with 2,2-dimethoxypropane is performed in acetone at room temperature.

Water is produced during the formation of a compound of the formula (11) and suitably is removed during the reaction by conventionnal methods, for example if toluene is used as a solvent by means of a Dean-Stark trap and if dichloromethane is used as a solvent by the addition of a suitable drying agent such as anhydrous magnesium sulphate.

The compound of the formula (12) is known from GB 1591723. The enantiomers of a compound of the formula (12) have not been previously described, however we have found that the (S)-enantiomer can be prepared following the methods described by R. W. Kierstead et al., J. Med. Chem. 26, 1561 (1983) and Y. Tsuda et al., Chem. Pharm. Bull., 29, 3593 (1981). Thus treatment of 1,2: 5,6-di-O-isopropylidene-D-mannitol with lead tetraacetate affords [R]-2,3-O-isopropylideneglyceraldehyde which is suitably successively reacted with 3,4-dimethoxyphenethylamine, a reducing agent such as sodium borohydride, and aqueous sodium hydroxide to afford (S)-3-[2-(3,4-dimethoxphenyl)ethylamino]-1,2-propanediol which is conveniently isolated as a hydrochloride salt.

The (S) isomer of a compound of the formula (12) is suitably converted via the (S) isomers of the compounds of the formulae (11), (5) and (6) wherein X is

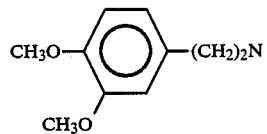

to afford the (S) isomer of the compound of the formula (4) using the methods as hereinbefore described.

In a further aspect this invention comprises compounds of the formulae (5) and (6) as hereinbefore defined.

The invention is illustrated by the following Scheme, Preparation and Examples.

SCHEME

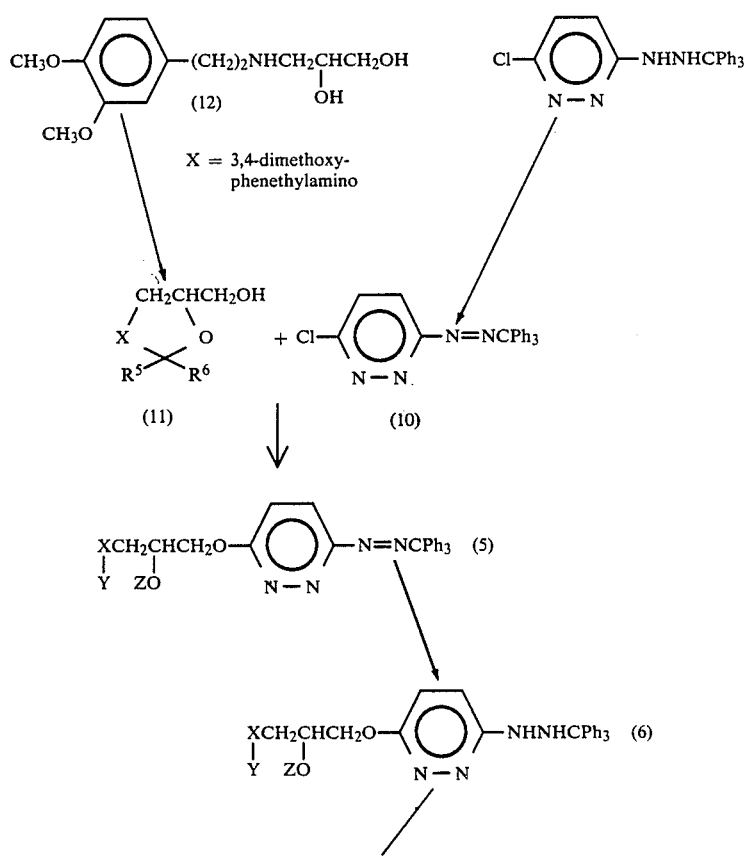

-continued
SCHEME

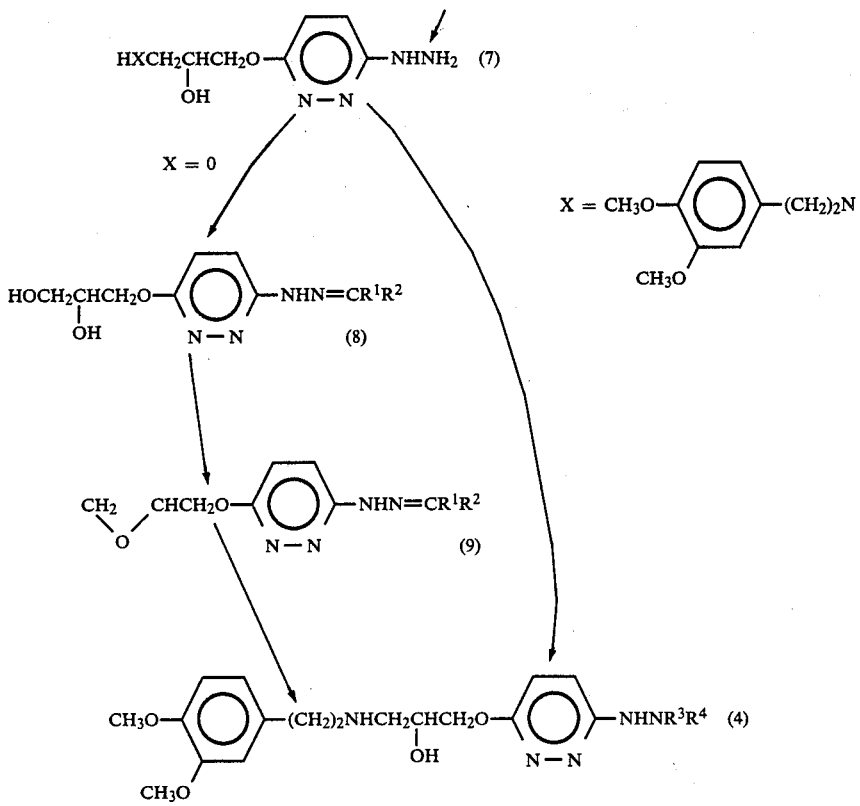

X, Y, Ph, Z, R$^1$ to R$^6$ are as hereinbefore defined.

PREPARATION 1

3-Chloro-6-triphenylmethylazopyridazine (a) To a solution of 25% aqueous hydrazine (4.25 l) and 32% ammonia (7.5 l) in water (23.7 l) 3,6-dichloropyridazine (3 kg) was added, while maintaining a gentle stream of nitrogen. The mixture was heated at reflux for 2 hours and, after cooling, the precipitate was collected, washed with water and dried to afford 2.5 kg (85.9%) of 3-chloro-6-hydrazinopyridazine, m.p. 140°-141° C.

(b) 3-Chloro-6-triphenylmethylhydrazinopyridazine was prepared in 84.8% yield from 3-chloro-6-hydrazinopyridazine as described in U.S. Pat. No. 4,575,552, which is herein incorporated by reference.

(c) To a mixture of 3-chloro-6-triphenylmethylhydrazinopyridazine (10 g) and cetyltrimethylammonium bromide (0.1 g) in dichloromethane (100 ml), 4% aqueous sodium hypochlorite (150 ml) was added. Stirring was continued at room temperature for 4 hours. The aqueous phase was removed and the organic layer was washed successively with dilute hydrochloric acid and water. After drying over anhydrous sodium sulfate the solvent was removed under vacuum and the residue was triturated with diisopropyl ether to yield 8.5 g of the title compound m.p. 123°-125° C. dec.

EXAMPLE 1

(RS)-1-[2-(3,4-Dimethoxyphenyl)ethylamino]-3-[3-(6-triphenylmethylazopyridazinyl)oxy]-2-propanol hydrochloride Method A To an ice cold solution of (RS)-3-[2-(3,4-dimethoxyphenyl)ethylamino]-1,2-propanediol bisulfate (250 g) in water (400 ml), a solution of 30% sodium hydroxide (156 ml) was added dropwise.

Isobutyraldehyde (72 ml) and dichloromethane (500 ml) were added and the mixture was vigorously stirred at 20° C. for 2 hours. The organic layer mixture was separated and dried overnight over 4A molecular sieves. These were removed by filtration, and the anhydrous filtrate was added to a solution of 3-chloro-6-triphenylmethylazopyridazine (258 g) in dichloromethane (1 liter).

A solution of potassium t-butoxide (82.5 g) in t-butanol (0.7 liter) was then added dropwise during 3 hours while maintaining the internal temperature between 0° and 4° C. Stirring was continued for 30 minutes, then 10% hydrochloric acid (400 ml) was added and the mixture was stirred at 20° C. for 15 minutes. The organic layer was separated, washed with brine and dried over sodium sulfate. Evaporation of the solvent gave a residue which was triturated with diisopropyl ether to afford 380 g of the title compound, m.p. 112° C. (with decomp). δ(DCl$_3$); 7.57 and 7.00 (ABq, 2H, J=9Hz, pyridazine-H), 7.40–7.00 (c.a., 15H, Ph-H), 6.75 (bs, 2H, NH$_2^+$), 6.60 (s, 3H, Ar-H), 5.00–4.40 (c.a., 4H, CHOH and OCH$_2$), 3.70 (s, 6H, OCH$_3$), 3.35–3.00 (c.a., 6H, CH$_2$CH$_2$N+CH$_2$)

Method B

A suspension of 3-[2-(3,4-dimethoxphenyl)ethylamino]-1,2-propanediol (13 g) and 2,2-dimethoxypropane (30 ml) in acetone (400 ml) was stirred at room temperature until a clear solution was obtained (about 24 hours). Evaporation of the solvent gave 15 g of 3-[2-

(3,4-dimethoxyphenyl)ethyl]-2,2-dimethyl-5-hydroxymethyloxazolidine, as an oily residue. This residue was dissolved in acetonitrile (500 ml) and to the stirred and ice-cold solution, 3-chloro-6-triphenylmethylazopyridazine (16 g) and sodium hydride (4 g, as a 50% suspension in oil) were added. Stirring was continued for one hour at room temperature, then 20% hydrochloric acid (20 ml) and brine (200 ml) were added, and the mixture stirred for one hour. The organic layer was separated and evaporated to dryness.

The residue was chromatographed over silica gel (WATERS PREP 500 preparative liquid chromatograph; eluant: dichloromethane-methanol 93:7) yielding 7.5 g of the title compound identical with that obtained according to Method A.

Method C

A mixture of 3-[2-(3,4-dimethoxyphenyl)ethylamino]1,2-propanediol (26 g), benzaldehyde (10.6 g) and a catalytic amount of p-toluenesulfonic acid in toluene (0.5 liter) was heated at reflux in a Dean-Stark apparatus for 4 hours. After cooling at room temperature, 3-chloro-6-triphenylmethylazopyridazine (34 g) was added at once and the mixture was stirred until solution. Sodium hydride (50% suspension in oil, 4.65 g) was then added portionwise and stirring was continued for 1.5 hours at room temperature. The reaction mixture was washed with water, the organic layer was separated, dried over MgSO4 and evaporated to dryness. The residue was dissolved with tetrahydrofuran (0.5 liter) and 100 ml of 1N hydrochloric acid were added.

The solution was stirred at room temperature for one hour and then evaporated to dryness. Trituration of the residue with diethyl ether afforded 40 g of the title compound identical with that obtained according to Method A.

EXAMPLE 2

(a)

(S)-3-[2-(3,4-Dimethoxyphenyl)ethylamino]-1,2-propanediol (i) To a solution of lead tetraacetate (17.5 g) in anhydrous toluene (100 ml), 1,2: 5,6-di-O-isopropylidene-D-mannitol (11 g) was added portionwise during 15 minutes, while maintaining a gentle stream of nitrogen. Stirring was continued at room temperature overnight. After the mixture was filtered through diatomaceous earth (Celite), the filter cake was washed with toluene and the filtrate was stirred with anhydrous sodium carbonate for 30 minutes. The precipitate was filtered off and the filtrate was treated with 2-(3,4-dimethoxyphenyl)ethylamine (7.6 g) and anhydrous potassium carbonate (22 g). After stirring for 2 hours at room temperature the precipitate was filtered off and the filtrate was evaporated to dryness under vacuum. The residue was dissolved in ethanol and sodium borohydride (4.4 g) was added portionwise during 1.5 hours while maintaining the temperature between 0° and 5° C. After stirring overnight at room temperature acetic acid was added to bring the pH to 4 and the solvent was removed under vacuum. The residue was dissolved in dichloromethne and washed with a saturated solution of sodium hydrogen carbonate. The aqueous phase was separated and extracted twice with dichloromethane. The combined organic phases were dried over anhydrous sodium sulfate and evaporated to dryness under vacuum to afford 19.7 g of (4S)-2,2-dimethyl-4-[[2-(3,4-dimethoxyphenyl)ethylamino]methyl]-1,3-dixolane as a brown oil. Treatement with an ethanolic solution of oxalic acid gave 13.6 g of the oxalate salt, m.p. 209°∝211° C. (decomp.), $[\alpha]_D = -21.1°$ (c=1, 50% acetic acid).

(ii) The above oxalate salt (14 g) was added to a stirred ice-cold mixture of 1N sodium hydroxide (75 ml) and dichloromethane (200 ml). After 30 minutes the phases were separated and the aqueous layer was extracted with dichloromethane (100 ml). The combined organic extracts were dried over anhydrous sodium sulfate and evaporated to dryness. The residue was dissolved into a 2.5% methanolic solution of hydrogen chloride and heated at 65° C. while distilling and continuously replacing the distillate with 2.5% methanolic hydrogen chloride. After 40 minutes the solvent was removed under vacuum and the residue was triturated with acetone to yield 6.7 g of the title compound as the hydrochloride, m.p. 92°–94° C.; $[\alpha]_D = -18.1°$ (c=1, EtOH).

(b)

(S)-1-[2-(3,4-Dimethoxyphenyl)ethylamino]-3-[3-(6-triphenylmethylazopyridazinyloxy]-2-propanol hydrochloride The title compound (5.1 g) was obtained by using the procedure described in Example 1 method A, starting from (S)-3-[2-(3,4-dimethoxyphenyl)ethylamino]-1,2-propanediol (3.8 g) and had m.p. 120° C. (with decomp), $[\alpha]_D = -3.7°$ (c=1, acetic acid).

EXAMPLE 3

(RS)-3-[3-[[2-(3,4-Dimethoxyphenyl)ethyl]amino]-2-hydroxypropoxy]-6-(2-triphenylmethylhydrazino)-pyridazine Method A Into a solution of 1-[2-(3,4-dimethoxyphenyl)ethylamino]-3-[3-(6-triphenylmethylazopyridazinyl)oxy]-2-propanol hydrochloride (380 g) in 95% ethanol (2 liters), containing 5% palladium on charcoal (40 g), a lively stream of hydrogen was bubbled for 8–10 hours at 20° C. and atmospheric pressure. The catalyst was filtered off, the filtrate was evaporated under vacuum to small volume, and diluted with ethyl acetate (1.5 liters). The resulting solution was extracted three times with 1N hydrochloric acid.

The aqueous extracts were neutralised with sodium hydrogen carbonate and extracted twice with dichloromethane. The organic layers were mixed, evaporated to dryness, and the residue was taken up in 95% ethanol (0.8 liter). The resulting solution was added dropwise to a vigorously stirred solution of sodium hydrogen carbonate (50 g) in water (5 liters). Stirring was continued for 30 minutes, then the precipitate was suction filtered to afford 332 g of the title compound, melting at 111° C. (with decomp); $\delta(CDCl_3)$; 7.50–7.18 (c.a., 16H, Ph-$\underline{H}$ and pyridazine H-5), 6.77 (A$\underline{B}$q, 1H, pyridazine H-4), 6.76 (s, 3H, Ar-H), 5.01 (bs, 1H, O$\underline{H}$), 4.50–4.00 (c.a., 3H, OC$\underline{H}_2$ and C$\underline{H}$OH), 3.80 (s, 6$\underline{H}$, OC$\underline{H}_3$), 3.30 (bs, 3H, C$\underline{H}_2$NH and N$\underline{H}$NHCPh$_3$), 3.00–2.60 (c.a., 6H, C$\underline{H}_2$CH$_2$NC$\underline{H}_2$).

Method B

To a solution of 1-[2-(3,4-dimethoxyphenyl)ethylamino]-3-[3-(6-triphenylmethylazopyridazinyl)oxy]-2-propanol hydrochloride (4.7 g) in tetrahydrofuran (30 ml) and ethanol (70 ml) were added 1N sodium hydroxide (8 ml) and 5% palladium on charcoal (0.8 g). Then sodium borohydride (0.7 g) was added portionwise, and stirring was continued at room temperature for 30 minutes. The catalyst was removed by filtration and the filtrate was diluted with water (200 ml). The precipitate was collected and dried to yield 3.2 g of the title compound, identical with that obtained according to Method A.

Method C

To an ice-cold suspension of stannous chloride (16.8 g) in water (130 ml) 50% aqueous sodium hydroxide (50 ml) was added dropwise while keeping the temperature under 10° C. The resulting solution was diluted with 95% ethanol (100 ml). To this, a solution of 1-[2-(3,4-dimethoxphenyl)ethylamino]-3-[3-(6-triphenylmethylazopyridazinyl)oxy]-2-propanol hydrochloride (23.2 g) in tetrahydrofuran (150 ml) was added dropwise, while maintaining the internal temperature between 0° and 7° C. Stirring was continued at room temperature for 15 minutes, then ethyl acetate (250 ml) was added. The organic layer was separated and the aqueous layer was extracted again with ethyl acetate (50 ml). The mixed organic layers were washed with brine and then diluted with cyclohexane (100 ml) and extracted twice with 1N hydrochloric acid (100+50 ml). The aqueous phases were mixed, neutralised with sodium hydrogen carbonate and extracted with dichloromethane. The organic phase was dried and evaporated to dryness. The residue was triturated with diisopropyl ether to afford 14.5 g of the title compound, identical with that obtained according to Method A.

EXAMPLE 4

S-3-[3-[[2-(3,4-Dimethoxyphenyl)ethyl]amino]-2-hydroxypropoxy]-6-(2-triphenylmethylhydrazino)-pyridazine The title compound (3.7 g) was obtained by using the procedure described in method A of Example 3 starting from the (S)-compound of Example 2(b) (5.1 g) and had m.p. 95° C. (with decomp); $[\alpha]_D = -4.1°$ (c=1, acetic acid).

EXAMPLE 5

(RS)-3-[3-[[2-(3,4-Dimethoxyphenyl)ethyl]amino]-2-hydroxypropoxy]-6-isopropylidenehydrazinopyridazine dihydrochloride A solution of 3-[3-[[2-(3,4-dimethoxyphenyl)ethyl]amino]-2-hydroxypropoxy]-6-(2-triphenylmethylhydrazino)pyridazine (330 g) and 37% hydrochloric acid (0.12 liter) in methanol (0.5 liter) and acetone (0.5 liter) was heated at reflux for 3 hours, then the solvent was evaporated under vacuum. The residue was diluted with n-butanol (100 ml), evaporated to dryness and triturated with acetone (1 liter) to afford 235 g of crude product which was dissolved in hot methanol (0.65 liter). The solution was filtered and diluted, while hot, with acetone (1.6 liter).

After standing overnight, the precipitate was collected and dried to yield 199 g of pure title compound melting at 210°-122° C. (with decomp).

EXAMPLE 6

(S)-3-[3-[[2-(3,4-Dimethoxyphenyl)ethyl]amino]-2-hydroxypropoxy]-6-isopropylidenehydrazinopyridazine dihydrochloride The title compound was obtained by using the procedure of Example 5 from the (S)-derivative of Example 4 and had m.p. 207°-210° C. (with decomp); $[\alpha]_D = 10.25°$ (c=1, EtOH). The enantiomeric purity (HPLC) was more than 96%.

EXAMPLE 7

(RS)-3-[3-[[2-(3,4-Dimethoxyphenyl)ethyl]amino]-2-hydroxypropoxy]-6-hydrazinopyridazine dihydrochloride A solution of 3-[3-[[2-(3,4-dimethoxphenyl)ethyl]amino]-2-hydroxypropoxy]-6-isopropylidenehydrazinopyridazine dihydrochloride (3 g) and 20% hydrochloric acid (200 ml) was evaporated to dryness at 25 mmHg pressure and maintaining the external bath at 40° C. The residue was crystallized from ethanol-isopropanol to afford 2 g of the title compound, m.p. 196°-198° C. (with decomp).

EXAMPLE 8

(RS)-3-[3-[[2-(3,4-Dimethoxyphenyl)ethyl]amino]-2-hydroxypropoxy-6-benzylidenehydrazinopyridazine dihydrochloride To a solution of (RS)-3-[3-[[2-(3,4-dimethoxyphenyl)ethyl]amino]-2-hydroxypropoxy]-6-hydrazinopyridazine dihydrochloride (2 g) in 40 ml of 90% aqueous methanol, (1 ml) of benzaldehyde was added. Stirring was continued at room temperature for two hours, then the solvent was evaporated under vacuum and the residue was triturated with isopropanol to afford the title compound in 80% yield, m.p. 207°-210° C. (with decomp).

EXAMPLE 9

(RS)-3-[3-[[2-(3,4-Dimethoxyphenyl)ethyl]amino]-2-hydroxypropoxy]-6-(2-methylpropylidene)hydrazinopyridazine dihydrochloride In a similar manner to Example 8 reaction of 2 g of (RS)-3-[3-[[2-(3,4-dimethoxyphenyl)ethyl]amino]-2-hydroxypropoxy]-6-hydrazinopyridazine dihydrochloride with (1.1 ml) of isobutyraldehyde afforded the title compound in 71% yield, m.p. 150°-152° C. (with decomp).

EXAMPLE 10

(RS)-3-[3-[2-(3,4-Dimethoxyphenyl)ethyl]-2-isopropyl-5-oxazolidinemethoxy]-6-(triphenylmethylazo)pyridazine To a solution of (RS)-3-[2-(3,4-dimethoxyphenyl)ethylamino]-1,2-propanediol (2.6 g) in dichloromethane (40 ml) was added isobutyraldehyde (11 ml) and anhydrous magnesium sulfate (10 g) and the suspension was stirred at room temperature for 2 hours. After filtration of inorganic matter, the filtrate was evaporated under vaccum, the residue was dissolved in anhydrous toluene and evaporated again to dryness. The residue was disloved in dichloromethane (40 ml), and to the solution, 3-chloro-6-triphenylmethylazopyridazine (3.5 g) was added. Then a solution of potassium t-butoxide (1.12 g) in t-butanol (10 ml) was added dropwise, keeping the internal temperature between 0° C. and 5° C. After stirring at room temperature for 2 hours, a saturated solution of ammonium sulfatte (50 ml) was added and the mixture was vigorously stirred for 10 min. The organic phase was separated, dried over MgSO$_4$ and evaporated to quantitatively afford the title compound as a reddish oily residue. Mass spectrum (E.I., 70 eV, 1.5 mA), m/z=629 (M-N$_2$)$^+$, 586 (M-C$_3$H$_7$-N$_2$)$^+$, 478 (M-C$_9$H$_{11}$O$_2$-N$_2$)$^+$, 338 (M-C$_{17}$H$_{25}$NO$_3$-N$_2$)$^+$, 243

(Ph$_3$C)$^+$. δ(CDCl$_3$): 7.75 (ABq, 1H, J=9Hz, pyridazine H-5), 7.45–7.00 (c.a., 16H, Ph-H and pyridazine H-4), 6.77 (s, 3H, Ar-H), 4.75–4.25 (c.a., 3H, CH$_2$O and CH-Pr-i), 4.15–4.00 (c.a., 1H, CHCH$_2$O), 3.85 (s, 6H, OCH$_3$), 3.35–2.60 (c.a., 6H, CH$_2$CH$_2$NCH$_2$), 1.90–1.60 [m, 1H, CH (CH$_3$)$_2$], 0.96 [d, 6H, J=6Hz, CH(CH$_3$)$_2$].

EXAMPLE 11

(RS)-3-[3-[2-(3,4-Dimethoxphenyl)ethyl]-2-isopropyl-5-oxazolidinemethoxy]]6-(2-triphenylmethylhydrazino)-pyridazine Into a solution of (RS)-3-[3-[2-(3,4-dimethoxyphenyl)ethyl]-2-isopropyl-5-oxazolidinemethoxy]-6-(triphenylmethylazo)pyridazine (6.5 g) in ethyl acetate (250 ml), containing 5% palladium on charcoal (1 g), hydrogen was bubbled for 12 hours. The catalyst was filtered off, the filtrate was washed with water (100 ml), dried over Na$_2$SO$_4$ and evaporated to dryness under vacuum. The residue was triturated with diisopropyl ether to yield 5 g of the title compound as an amorphous solid, m.p. 92°–95° C. (with decomposition). Mass spectrum (E.I., 70 eV, 1.5 mA), m/z=586 (M-C$_3$H$_9$-N$_2$)$^+$, 478 (M-C$_9$H$_{13}$O$_2$-N$_2$)$^+$, 338 (M-C$_{17}$H$_{27}$NO$_3$-N$_2$)$^+$, 243 (Ph$_3$C)$^+$. δ(CDCl$_3$): 7.70–7.10 (c.a., 16H, Ph-H and pyridazine H-5), 6.80–6.70 (c.a., 4H, ArH and pyridazine H-4), 5.95 and 4.87 (bs, 2H, NHNH), 4.70–4.00 (c.a., 5H, OCH$_2$, N-CH-O, O-CHCH$_2$ and OH), 3.83 and 3.84 (s, 6H, OCH$_3$), 3.20–2.30 (c.a. 6H, CH$_2$CH$_2$NCH$_2$), 2.00–1.55 (m, 1H, CH$_3$-CH-CH$_3$), 1.00–0.85 (m, 6H, CH$_3$-CH-CH$_3$).

EXAMPLE 12

(RS)-3-[3-[[2-(3,4-Dimethoxyphenyl)ethyl]amino]-2-hydroxypropoxy]-6-(2-triphenylmethylhydrazino)-pyridazine To a solution of (RS)-3-[3-[2-(3,4-dimethoxphenyl)ethyl]-2-isopropyl-5-oxazolidinemethoxy]-6-(2-triphenylmethylhydrazino)pyridazine (5 g) in tetrahydrofuran (100 ml), 20% hydrochloric acid (3 ml) was added. After stirring at room temperature for 15 minutes the solvent was removed under vacuum. The residue was dissolved in dichloromethane (50 ml) and washed three times with a saturated solution of sodium hydrogen carbonate (30 ml). The organic phase was dried over Na$_2$SO$_4$ and evaporated to dryness. The residue was triturated with diisopropyl ether to afford 3.1 g of the title compound, identical with that obtained in Example 3.

EXAMPLE 13

(RS)-3-(2,2-Dimethyl-1,3-dioxolan-4-methoxy)-6-(triphenylmethylazo) pyridazine

To a stirred suspension of 50% sodium hydride (10.3 g) in anydrous toluene (750 ml), 2,2-dimethyl-4-hydroxymethyl-1,3-dioxolane (30 ml) was added dropwise. Stirring was continued at room temperature for 30 minutes, then 3-chloro-6-triphenylmethylazopyridazine (72 g) was added in four portions during one hour, while keeping the internal temperature under 30° C. After 90 minutes, the mixture was washed twice with water (150 ml), dried over MgSO$_4$ and evaporated to dryness. The residue was triturated with cyclohexane to yield 73.5 g of the title compound as a yellow solid, m.p. 119°–120° C.

EXAMPLE 14

(RS)-3-(2,3-Dihydroxypropoxy)-6-isopropylidenehydrazinopyridazine hydrochloride

To a stirred solution of 3-(2,2-dimethyl-1,3-dioxolan-4-methoxy)-6-(triphenylmethylazo)pyridazine (73.5 g) in tetrahydrofuran (225 ml) and ethanol (350 ml), 5% palladium on charcoal (7.5 g) was added then sodium borohydride (7.5 g) was added portionwise during one hour. Stirring was continued for 45 minutes, then the reaction mixture was diluted with water (1.25 liter) to afford a precipitate comprising the intermediate, (RS)-3-[2,2-dimethyl-1,3-dioxolan-4-methoxy]-6-(2-triphenylmethyl hydrazino)pyridazine, mixed with the catalyst. The precipitate was filtered by suction and dissolved in ethanol (200 ml) containing concd. hydrochloric acid (19 ml). The mixture was filtered through a Celite pad and the clear filtrate was concentrated to small volume under vacuum. The residue was diluted with acetone, evaporated to small volume and diluted again with acetone (750 ml). The solution was stirred at room temperature for 0.5 hours then at 0° C. for 1 hour to precipitate 34.7 g of the title compound as a white solid, m.p. 188°–190° C.

The intermediate, (RS)-3-[2,2-dimethyl-1,3-dioxolan-4-methoxy]-6-(2-triphenylmethylhydrazino)pyridazine (m.p. 159°–162° C.) can be isolated by dissolving the precipitate mixed with the catalyst in tetrahydrofuran, filtering off the catalyst, evaporating to dryness and triturating the residue with diisopropyl ether.

EXAMPLE 15

(RS)-3-(2,3-Epoxypropoxy)-6-isopropylidenehydrazinopyridazine

A mixture of 3-(2,3-dihydroxypropoxy)-6-isopropylidenehydrazinopyridazine hydrochloride (34.7 g), acetic acid (50 ml) and 33% hydrogen bromide in acetic acid (143 ml) was stirred at room temperature for 2 hours, and diluted with diisopropyl ether (1.5 liter). After 30 minutes the precipitate was collected, protecting it from moisture with dry nitrogen, and dried under vacuum at room temperature. The solid was dissolved with methanol (600 ml) and heated at reflux for 2 hours. After stirring at room temperature for 15 hours, the solvent was removed under vacuum and the residue was diluted with acetone and evaporated again to dryness. To the residue were added dichloromethane (400 ml), cetyltrimethylammonium bromide (3.4 g) and, with vigorous stirring and keeping the internal temperature under 10° C., 2N sodium hydroxide (100 ml). Stirring was continued at room temperature for 90 minutes, then the phases were separated and the organic layer was washed with water (2×200 ml), then with a saturated solution of ammonium sulfate (135 ml). The organic solution was dried over MgSO$_4$, evaporated under vacuum and the residue was triturated with diisopropyl ether (200 ml) to yield 20 g of the title compound as a pale yellow solid, m.p. 106°–109° C. (with decomposition).

EXAMPLE 16

(RS)-3-[3-[[2-(3,4-Dimethoxyphenyl)ethyl]amino]-2-hydroxypropoxy]-6-isopropylidenehydrazionpyridazine dihydrochloride A mixture of 3-(2,3-epoxypropoxy)-6-isopropylidenehydrazinopyridazine (20 g) and 3,4-dimethoxyphenethylamine (40 ml) was stirred at 50° C. for 4 hours. After cooling, the mixture was dissolved in dichloromethane (100 ml) and poured into diisopropyl ether (800 ml). After stirring for 1 hour the precipitate was collected and triturated with diisopropyl ether (400 ml). The collected solid was dissolved in ethanol (300 ml) and 5.4N hydrochloric acid (35 ml) was added dropwise. The solvent was evaporated under vacuum, the residue was diluted with acetone (100 ml) and toluene (100 ml) and evaporated to dryness. The residue was crystallised from ethanolacetone to afford 26.6 g of the title compound as a pale yellow solid, m.p. 206°–209° C. (with decomposition).

EXAMPLE 17

(RS)-3-(6-Triphenylmethylazo-3-pyridazinyl)oxy]-1,2-propanediol

A solution of (RS)-3-(2,2-dimethyl-1,3-dioxolan-4-methoxy)-6-(triphenylmethylazo)pyridazine (7 g) in a mixture of 95% ethanol (40 ml) and tetrahydrofuran (30 ml) containing 10% hydrochloric acid (2 ml) was stirred at room temperature for 24 hours. The solvent was evaporated under vacuum and the residue was crystallized from isopropanol to afford 4.2 g of the title compound as a yellow solid, m.p. 132°–134° C. (with decomposition). $\delta$(DMSO-$d_6$), =7.95 (AB q, 1H, J=9Hz, pyridazine H-5), 7.43–7.04 (c.a., 16H, Ph-H+pyridazine H-4), 4.98 (d, 1H, J=5Hz, CHOH), 4.70 (t, 1H, J=5Hz, $CH_2OH$), 4.75–4.35 (m, 2H, $OCH_2$), 4.05–3.70 (m, 1H, CHOH), 3.52 (dd, 2H, J'=J" 5Hz, $CH_2OH$). Mass spectrum (E.I. 70 eV, 1.5 mA), m/z=412 (M-$N_2$)+, 337 (M-$C_3H_7O_2$-$N_2$)+, 244 ($Ph_3CH$)+, 243 ($Ph_3C$)+.

EXAMPLE 18

(RS)-3-(2,3-Dihydroxypropoxy)-6-(2-triphenylmethylhydrazino)pyridazine

Into a solution of (RS)-3-[(6-triphenylmethylazo-3-pyridazinyl)oxy]-1,2-propanediol (5.45 g) in 95% ethanol (100 ml) and tetrahydrofuran (50 ml) containing 5% palladium on charcoal (1.1 g) hydrogen was bubbled, at room temperature, for 16 hours. Removal of the catalyst and evaporation of the solvent gave a residue which was crystallized from 2-propanol to yield 3.2 g of the title compound, m.p. 174°–176° C. Mass spectrum (E.I. 70 eV, 1.5 mA), m/z=412 (M-$N_2H_2$)+, 338 (M-$C_3H_8N_2O_2$)+, 243 ($Ph_3C$)+.

EXAMPLE 19

(RS)-3-(2,3-Dihydroxypropoxy)-6-isopropylidenehydrazinopyridazine hydrochloride

To a solution of (RS)-3-(2,3-dihydroxypropoxy)-6-(2-triphenylmethylhydrazino)pyridazine (3.2 g) in tetrahydrofuran (80 ml), conc. hydrochloric acid (2 ml) was added. After stirring at room temperature for 15 minutes the solution was concentrated under vacuum to small volume and diluted with acetone (50 ml). After stirring at room temperature for 30 minutes and then at 0° C. for 1 hour the precipitate was collected to yield 1.4 g of the title compound, identical to that obtained in Example 14.

What is claimed is:
1. A process for preparing a compound of the formula (4), or a pharmaceutically acceptable salt thereof:

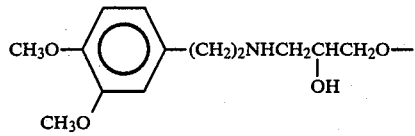
(4)

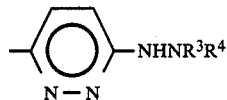

wherein
$R^3$ and $R^4$ are both hydrogen or together are =$CR^1R^2$
where
$R^1$ is hydrogen or $C_{1-3}$ alkyl and
$R^2$ is $C_{1-3}$alkyl, carboxy or phenyl,
which process comprises:
(a) adding hydrogen to the double bond of a compound of the formula (5):

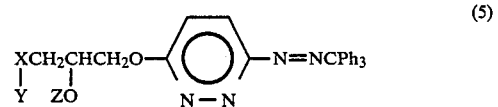
(5)

wherein
X is

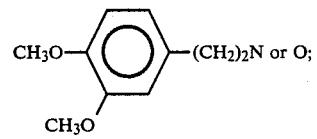

Y and Z are both hydrogen or
Y and Z together are a protecting group

wherein
$R^5$ is hydrogen or $C_{1-3}$alkyl and $R^6$ is $C_{1-3}$alkyl or phenyl, and
Ph is phenyl,
to afford a compound of the formula (6):

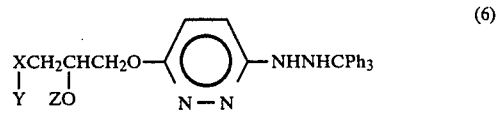
(6)

wherein Ph, X, Y and z are as hereinbefore defined, and
(b) removing by acid catalyzed hydrolysis the triphenylmethyl group, the

group and any other protecting groups added in the reaction in step (a) to afford a compound of the formula (7) or an acid-addition salt thereof:

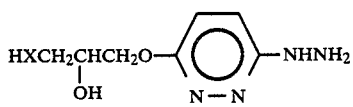 (7)

wherein X is as hereinbefore defined.
(c) when X is

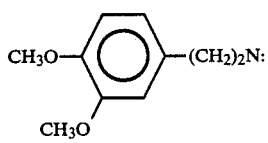

reacting a compound of formula (7) with $R^1R^2CO$ wherein $R^1$ and $R^2$ are as hereinbefore defined to yield a compound of the formula (4):
or when X is O:
reacting a compound of formula (7) with $R^1R^2CO$ wherein $R^1$ and $R^2$ are as hereinbefore defined to afford a compound of the formula (8):

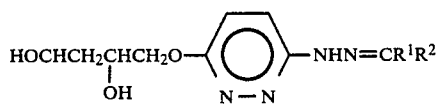

wherein $R^1$ and $R^2$ are as hereinbefore defined which is converted by treatment with hydrogen bromide in acid, followed by treatment with a base to a compound of the formula (9):

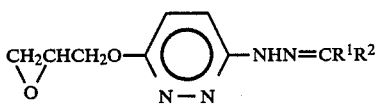

wherein $R^1$ and $R^2$ are as hereinbefore defined which is reacted with 3,4-dimethoxyphenethylamine, and thereafter removing the $CR^1R^2$ group by hydrolysis, to yield a compound of formula (4).

2. A process according to claim 1 wherein X is O and Y and Z are together a protecting group $CR^5R^6$ as defined in claim 1.

3. A process according to claim 1 wherein X is

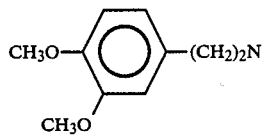

and Y and Z are both hydrogen.

4. A process according to claim 1 wherein the reducing agent is selected from hydrogen with palladium on carbon, sodium borohydride with palladium on carbon, sodium hydrosulphite, and an aqueous mixture of stannous chloride and sodium hydroxide.

5. A process according to claim 1 wherein the reduction of a compound of the formula (5) is performed in a solvent, such as a $C_{1-4}$alkanol or tetrahydrofuran or mixtures thereof, at a temperature from 0° to 50° C.

* * * * *